(12) United States Patent
Goldstein

(10) Patent No.: US 6,506,175 B1
(45) Date of Patent: Jan. 14, 2003

(54) THERAPEUTIC BANDAGE

(76) Inventor: Samuel A. Goldstein, P.O. Box 1215, West Chester, PA (US) 19380

( * ) Notice: Subject to any disclaimer, the term of this patent is extended or adjusted under 35 U.S.C. 154(b) by 0 days.

(21) Appl. No.: 09/539,091

(22) Filed: Mar. 30, 2000

Related U.S. Application Data

(63) Continuation-in-part of application No. 09/276,875, filed on Mar. 26, 1999, now abandoned.

(51) Int. Cl.⁷ .................................. A61F 13/00
(52) U.S. Cl. ...................... 602/60; 602/61; 602/62
(58) Field of Search .................. 602/60–62, 64–66, 602/75, 20, 23, 26, 44; 2/455, 456, 22, 24

(56) References Cited

U.S. PATENT DOCUMENTS

| | | | |
|---|---|---|---|
| 5,085,209 A | 2/1992 | Gottschalk | 606/201 |
| 5,139,476 A | 8/1992 | Peters | 602/26 |
| 5,254,122 A | 10/1993 | Shaw | 606/201 |
| 5,385,538 A | 1/1995 | Mann | 602/26 |

*Primary Examiner*—Kim M. Lewis
(74) *Attorney, Agent, or Firm*—Duane Morris LLP

(57) ABSTRACT

An orthopedic bandage includes a length of unbroken loop fabric to which a layer of thermoplastic breathable elastomeric foam is intimately adhered. The bandage has integral or attachable parts of different widths that are closed around an anatomical part using tabs that engage the fabric where desired, in a hook-and-pile fastener arrangement. Narrower strap-like parts and wider pad-like parts which can have specific shapes, wrap around the body with minimal bunching or folding which allow a user to apply desired amount of concentrated and general pressure around the particular areas of the body. In addition, the wide and narrow straps are effective to engage tapering anatomical parts such as the base of the hand and wrist or the ankle and foot.

12 Claims, 20 Drawing Sheets

THERAPEUTIC BANDAGE

CROSS REFERENCE TO RELATED APPLICATIONS

This is a continuation-in-part of U.S. application Ser. No. 09/276,875, filed Mar. 26, 1999, now abandoned.

BACKGROUND OF THE INVENTION

1. Field of the Invention

The invention relates generally to the field of elasticized orthopedic devices applied on or about portions of the body for compression, support, protection, therapeutic effect and the like. More particularly, a reusable, bonded, urethane-based thermoplastic foam layer is intimately adhered to an elasticized fabric substrate having certain fastening structures and properties. According to an inventive aspect, the fabric and bonded foam define flat strap and pad portions having different widths, arranged such that the device conforms to specific body portions for compression and support with minimal bunching or folding. In particular the invention is arranged to conform to a user's limbs and joints. The structure of the fabric and bonded foam and the fastening structures permit wrap-backs and overlaps. More or less tension can be applied up to a point of attachment, for adjusting the intensity at localized areas with gradient pressure. Electrically formed heat-welded seams bond parts of the device, including the hook parts of hook-and-loop fastening elements that engage at a user selected position on the fabric to adjust and affix the device in place.

2. Prior Art

For various reasons, for example due to trauma, illness, weakness or age, or simply to provide additional resistance to strains, the muscles, joints, and soft tissue of the human body can benefit from added exterior compression and support. This may be the case for mundane functions such as walking, running, throwing and the like, for physically demanding functions such as weight lifting, for repetitive motions such as typing, etc. To be compatible for use on the human anatomy, applied supports have traditionally taken the form of some type of stretch fabric which is wrapped around the portion of the user's body that is required to be reinforced and supported, for example, the ankles, knees, wrists, elbows, shoulders, lumbar region, thighs or digits as well as the soft tissue that adjoins and surrounds these regions of the body. Elasticized tubular structures also have been produced in suitable size and shape for use about the knees, wrists, etc. Conventional tubular structures that might exert effective pressure can be difficult to get on and off, or to pull into place, or to keep in position. Tubular structures generally lack adjustability, and may not exert the most desirable amount of pressure at the point where they are placed, due to the relative sizes of the tubular support structure and the user's body. Every user's body is substantially unique in its dimensions, at a level of precision that is needed to provide a convenient yet effective support.

A support as described may be used for purposes of therapeutic support, such as to protect and support tissues that already have been injured or weakened, or for prophylactic use, i.e., to prevent an injury. Such supports may be used to ensure safety during a particularly vigorous form of exercise, to carry a supporting or impact-absorbing structure, or simply for the user's comfort. Although discussed herein with reference to support of the human body, and in particular to support joints and appendages, the invention is broadly applicable to other sites on the human body as well as to veterinary uses and the like.

A popular form of support for a muscle or joint is an elongated length of resiliently stretchable (e.g., elasticized) fabric, known as an "Ace" bandage. The Ace type bandage is versatile in that the same form of bandage can be wrapped around various different portions of the body when necessary, by suitably encircling the affected body portion using the simple elongated strip-like bandage. Thus the bandage can be wrapped around irregularly shaped portions of the anatomy, for example, arches, ankles, knees, elbows and the like. The bandage is wrapped with some elastic elongation, in repeated turns of the fabric over and around the affected portion, until the area requiring support is adequately covered and adequate resilient pressure is applied. After the strip-like bandage is wrapped around the affected body portion, the free end of the bandage is secured against a previous wrap. This can be accomplished by butterfly clips that engage in the fabric, by tucking under the free end or other by another fastening method or device that prevents unraveling of the wraps.

U.S. Pat. No. 5,036,838—Sherman discloses an improved foam plastic orthopedic bandage which is simple in design, inexpensive to manufacture and efficient in use. The bandage comprises a layer of unbroken-loop fabric which may be elasticized. The unbroken loop fabric has fastening properties similar to the pile side of a hook-and-pile fastener (e.g., "VELCRO" brand or a similar material) such that the hook side of such a fastener can be used to affix a free end of the bandage to an overlapped layer. The unbroken loop fabric when utilized in a support device, can be either stretchable with elasticity both in the longitudinal direction and in the transverse direction or non-stretchable. A second stretchable foam plastic layer is intimately bonded to the unbroken loop fabric layer or sheet without the need for additional materials such as stitching, rivets, staples, etc. in an automatic, heat applied, bonding process. The foam layer is non-cytotoxic, breathable, and of sufficient thickness to provide satisfactory cushioning over the portion of the human body to be treated with the orthopedic bandage.

Although the '838 patent provided an improved foam plastic orthopedic bandage, it was limited to a generally elongated strip structure similar to an Ace bandage. In U.S. Patent Des.383,846—Goldstein, the foam plastic bandage concept is embodied in a bandage or support structure having a central panel of relatively greater width with adjoining lengths extending in opposite directions from the central panel, and tapering to narrow ends. One of the ends bears a fastener that can engage at any point on one face of the composite foam/fabric material (namely on the fabric side. This bandage is disclosed for use, for example, as a foot and ankle support; however its structure and concept are similar to an Ace bandage in that it is a generic-shaped piece of material can be wrapped around a body part and affixed as desired by joining a free end to the underlying wrap(s). It would be advantageous if such a bandage could be improved for particular uses such as specific joints and appendages, optimized for such uses and nevertheless arranged to adjust precisely in a manner appropriate for the location and the extent of support required by the user.

SUMMARY OF THE INVENTION

The invention concerns elasticized orthopedic devices that are wrapped about portions of the body and affixed at least at one free overlapping end, for applying compression, pressure and support to the tissues and to support joints, such as, ankles, elbows, knees, and wrists. More particularly, a reusable, bonded, plastic foam layer is intimately adhered to an elasticized fabric substrate having fastening properties.

The overlapping portions of fabric are provided in varying widths and shapes that can be endwise attached to one another. Wider shapes are useful in wrapping around specific portions of the body to provide a relatively wide area of supporting pressure, and the narrower shapes concentrate additional support at a selected area, for example overlapping or underlapping the wider part, or engaging adjacent to a protruding anatomical area such that the adjustable device is fixed in is place as well as adjustable for the user's particular size and the extent of pressure required.

The foam plastic and fabric device preferably comprises a thermoplastic urethane foam layer that has been intimately adhered to an elasticized substrate fabric. Such adherence is aptly provided by curing a liquid foam composition that is poured or flowed onto one side of the fabric such that the curing foam engages the interstices of the fabric upon curing, while leaving strands of the fabric exposed on the opposite side, including unbroken strands that provide the functional loop or pile structure needed for engagement with the hook side of a hook-and-pile fastener. Thus the substrate preferably comprises an unbroken loop or strand fabric and has fastening properties resembling those of the pile side of a hook and pile fastener. Tabs that are faced with the corresponding hooks of a hook and pile type fastener are attached to the device, preferably at least at one free edge of the wider or narrower shapes, for example being electronically welded to the fabric and underlying foam layer at the end of a narrower over-wrap portion. The tabs can be quickly fastened to the fabric with minimal pressure or released from the surface of the fabric by being pulled upward from engagement, enabling the device to be fit precisely, or to be refit afterwards (e.g., tightened, loosened, repositioned, etc.). The device accommodates the dimensions of any user over a wide range of sizes, and provides the desired degree of resilient pressure for each. The tabs can be affixed anywhere over the available span of fabric to achieve a wide variety of different configurations, with certain particular configurations being discussed below for relief of common complaints or for supporting particularly vulnerable anatomical structures.

The thermoplastic foam layer provides a cushioning support device that breathes, for comfortable, direct contact with the skin, and can even be used over an open wound. Different examples of the invention can be used singularly or in combination, on the ankles, feet, knees, wrists, hands, elbows and the like.

It is therefore an object of the invention to provide improved foam plastic orthopedic bandages having the attributes set forth.

It is another object to provide improved foam plastic orthopedic bandages which may be used to treat and/or to obviate the symptoms of carpal tunnel syndrome, tennis elbows, injuries to the Achilles tendon and similar traumatic conditions located around ankles, wrists, and knees, as well as generally to provide comfortable, well fitting and protective support to the ankles, wrists and other anatomical parts which can benefit from added exterior support.

Other objects and aspects of the invention will be apparent from the following description of certain exemplary embodiments in conjunction with the accompanying drawings.

BRIEF DESCRIPTION OF THE DRAWINGS

Shown in the drawings are exemplary embodiments of the invention as presently preferred. It should be understood that the invention is not limited to only these embodiments but is capable of variation within the scope of the appended claims. In the drawings:

DETAILED DESCRIPTION OF THE PREFERRED EMBODIMENTS

Figure 1:
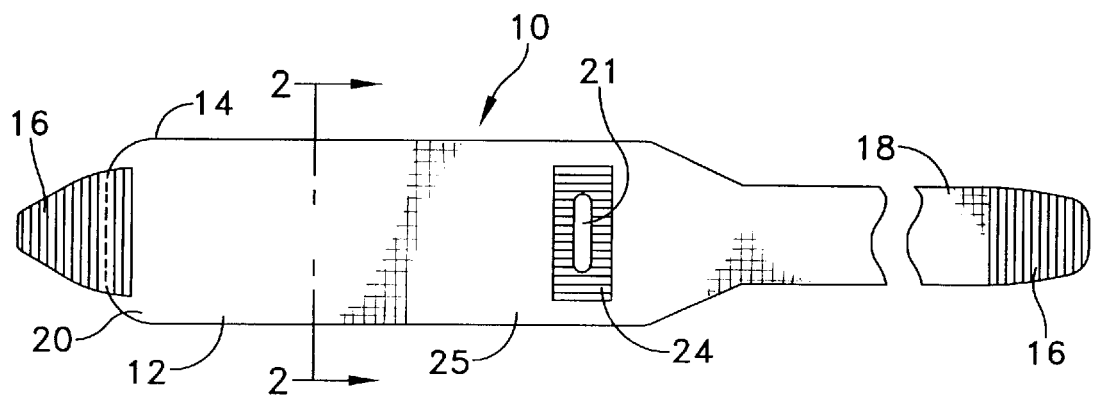
FIG. 1 is a top plan view of the foam plastic orthopedic bandage of the invention.
Figure 2:
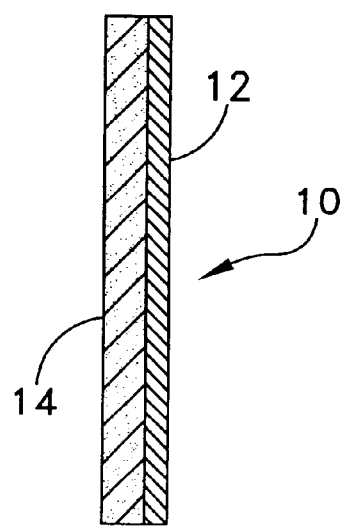
FIG. 2 is an enlarged, cross-sectional view taken along line 2—2 on FIG. 1, looking in the direction of the arrows.

Referring to FIGS. 1 and 2, orthopedic bandage 10 comprises a layer of loop fabric 12 and a layer of plastic 14. Preferably, loop fabric 12 is elasticized, and has fastening properties similar to the loop side of a hook-and-loop fastener pair, namely exposed unbroken loops or lengths of fiber over a span permitting the fiber to be engaged by the hook side of such a fastener pair. As seen in FIG. 2, a first layer comprising fabric layer 12 is permanently affixed to second layer 14, which is made of a stretchable foam plastic. Foam plastic layer 14 can comprise a urethane foam that is securely bonded to fabric layer 12. In one embodiment of the invention, foam plastic layer 14 and fabric layer 12 are attached by adhesive or by electrical welding. In another embodiment, foam plastic layer 14 is formed from a blown liquid polymer that is poured onto fabric layer 12 and cured in situ. In this embodiment, the liquid polymer penetrates the interstices of the fabric prior to curing, thereby creating a secure bond. It is preferred that no additional fasteners, such as, stitching, rivets, staples, etc., be required or used to adhere fabric layer 12 to foam plastic layer 14. According to another embodiment, the foam is specifically thermoplastic urethane foam and the fabric is adhered to the foam in an automatic bonding process involving heating the fabric (and the foam through the fabric), to soften the foam and achieve a similar interstitial bonding between the foam and the fabric.

As seen in FIG. 1, the layer of fabric 12 includes a first end 18 and a second end 20. First end 18 is disposed along a thinner strap-like section and second end 20 is disposed along a wider pad-like section. A transverse opening 22 is provided in second end 20 (wider section), and is dimensioned such that the narrower strap-like section (first end 18) can be looped over and passed through opening 22. Opening 22 is bounded by a reinforcing strip 24, which may comprise a tab of plastic that is heat bonded to fabric layer 12 and a portion of foam plastic layer 14 that bleeds through fabric layer 12 during welding. For example, reinforcing strip 24 may comprise hook-type fastening material which is permanently affixed to fabric layer 12 by heat sealing. The hooks are arranged to engage foam plastic layer 14 through fabric layer 12 behind it.

Fastening tabs 16 are provided on first end 18 and second end 20, and are formed of hook-type fastening material that is adapted to engage and hold fabric layer 12 when bandage 10 is stretched and wrapped, as will hereinafter be disclosed in further detail. Fastening tabs 16 comprise short lengths of plastic hook material, which may be heat sealed at each end of the device. Fastening tabs 16 have hook material surfaces extending beyond the extreme ends of bandage 10. The hook material is oriented so that when bandage 10 is stretched taut around an anatomical part, and tab 16 is pressed against fabric layer 12, the hooks engage fabric layer 12 and lock bandage 10 taut in place. It is possible to place a tab 16 at only one end; however, tabs 16 are preferably provided at both ends of fabric layer 12 and stretchable foam plastic layer 14.

A portion 25 of bandage 10, disposed between first end 18 and second end 20, is wider than first end 18. In this way, transverse opening 22 may be provided in bandage 10 so as to be at least as wide as first end 18. As a result, first end 18 may be wrapped around a body part and threaded through opening 22.

The preferred embodiment of bandage 10 comprises two different widths along its length. It would be possible, however, to employ additional distinct widths along the length bandage 10. When bandage 10 is wrapped about a body part, with selected resilient stretching, inward pressure is more concentrated under the thinner-width portions of bandage 10, and less concentrated under the thicker-width portions. Different constructions are possible but in the embodiment shown the thicker-width portion is intended either to overly the thinner-width portion, or the thicker-width portion may wrap around one anatomical part and the thinner-width portion may wrap around an adjacent anatomical part. This arrangement positions the respective thicker and thinner portions of bandage 10, securely and comfortably without folding and bunching.

Figure 1A:
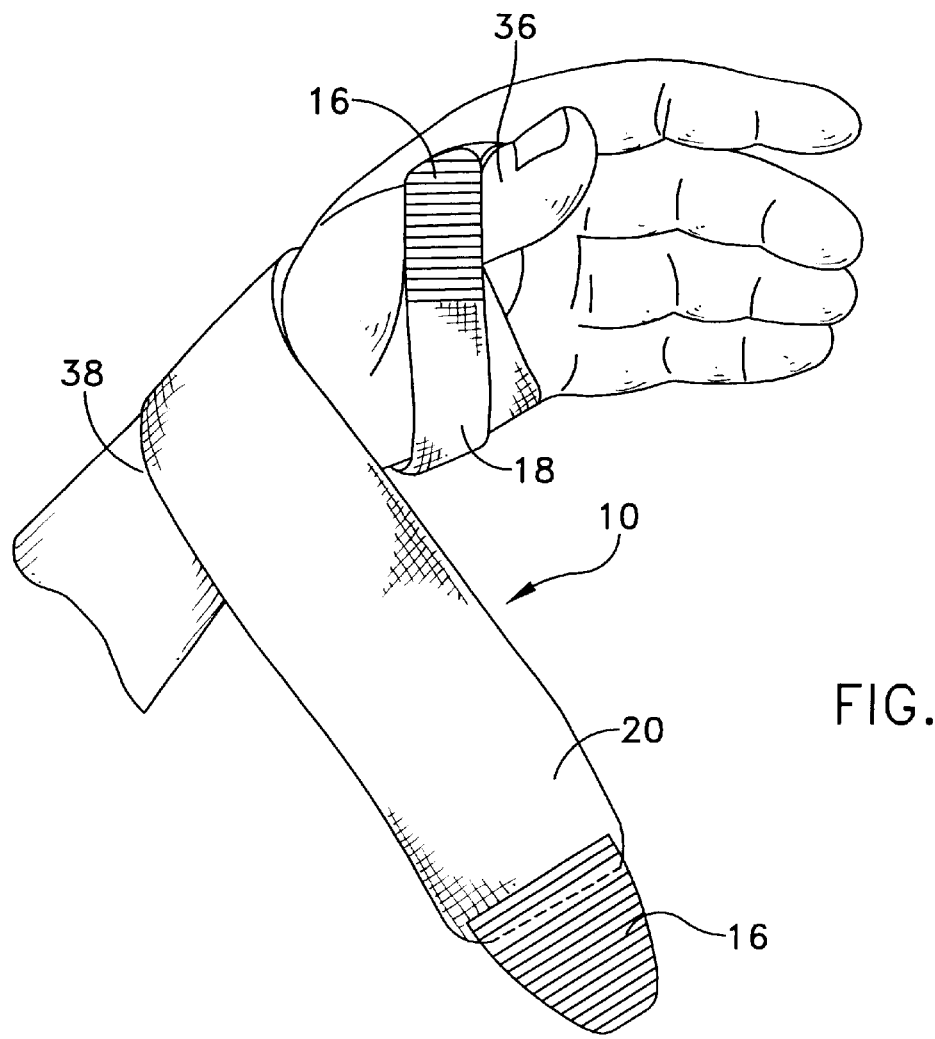
FIG. 1A is a perspective view showing the orthopedic bandage of FIG. 1 in the process of being wrapped around a wrist and thumb.
Figure 1B:
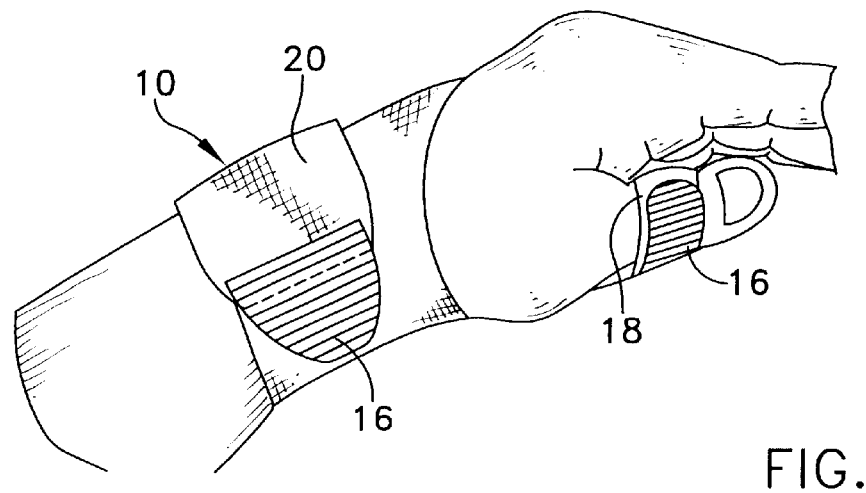
FIG. 1B shows the result of the wrapping shown in FIG. 1A.

As shown in FIGS. 1A and 1B, bandage 10 can be wrapped around the base of the hand to encompass and lock around the wrist 38 and the tapering proximal part of the wearer's hand, with tab 16 on second end 20 of bandage 10 locking back against itself. The thinner portion encircles the base of thumb 36 and attaches back to the wider portion of bandage 10, via tab 16 at first end 18.

As shown in FIG. 1A, after first end 18 of bandage 10 is threaded through transverse opening 22 (not shown in this figure) and first end 18 is wrapped around thumb 36, tab 16 of first end 18 is secured to a receiving portion of first end 18. Second end 20 of bandage 10 is shown partially wrapped around wrist 38 FIG. 1B shows second end 20 completely wrapped around wrist 38 and tab 16 of second end 20 secured to the receiving portion of second end 20. The arrangement as shown can be wrapped at the user's choice further up over the hand, for example to support the wrist for alleviating carpal tunnel pain, or further away from the hand, for example to support a sprained wrist. In addition, more or less pressure can be exerted, as desired, by exerting corresponding tension (stretching force), when wrapping bandage 10. With more or less tension and stretching, the position at which tabs 16 attach to underlying fabric layer 12 is moved circumferentially farther or less far.

Figure 1C:
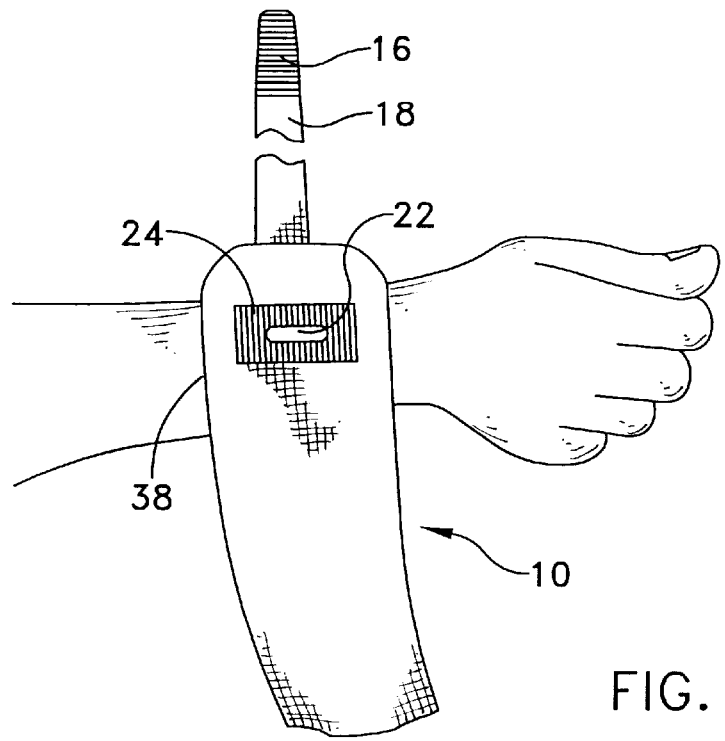
FIGS. 1C, 1D and 1E are top perspective views showing the orthopedic bandage of FIG. 1 being wrapped around a wrist such that the wider and narrower portions engage and overlap.
Figure 1D:
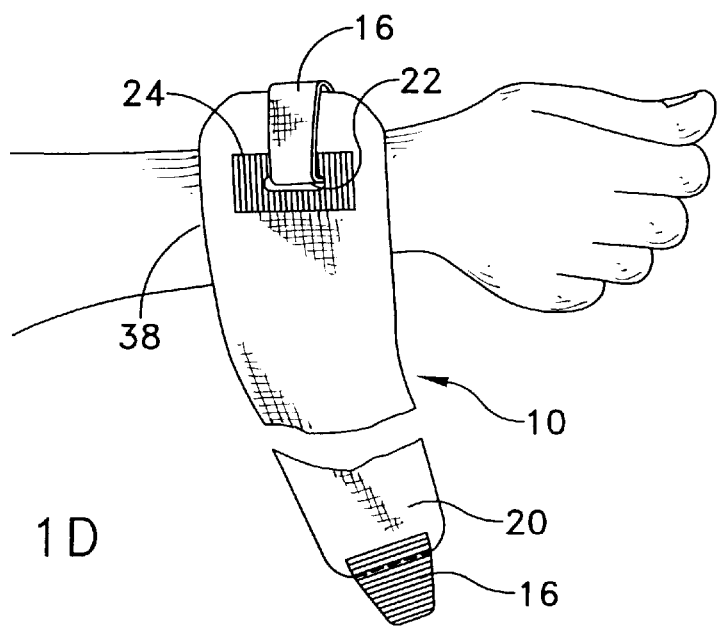
Figure 1E:
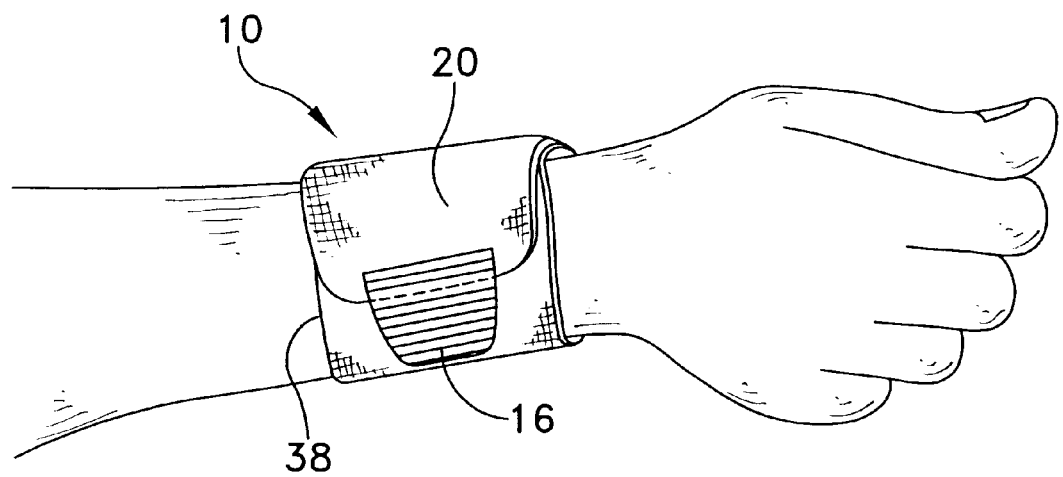

FIGS. 1C, 1D and 1E show an alternative use of bandage 10 of FIG. 1 to concentrate the pressure exerted on a more or less cylindrical anatomical part, such as the wrist or forearm. The wider section of bandage 10 exerts a distributed force and/or acts as an outer pad; and the narrower section of bandage 10 exerts a concentrated force which may be selected by the user. As shown in FIG. 1C and 1D, when wrapping bandage 10 around wrist 38, first end 18 threaded through transverse opening 22 and tab 16 (not shown) of first end 18 is secured to a receiving surface defined by the portion of fabric layer 12. FIG. 1E shows second end 20 of bandage 10, (wider section), wrapped completely around wrist 38 with tab 16 secured to the receiving surface defined by a portion of fabric layer 12 that is facing the wider section of bandage 10, and which section overlies the affixed narrower strap section.

Figure 1F:
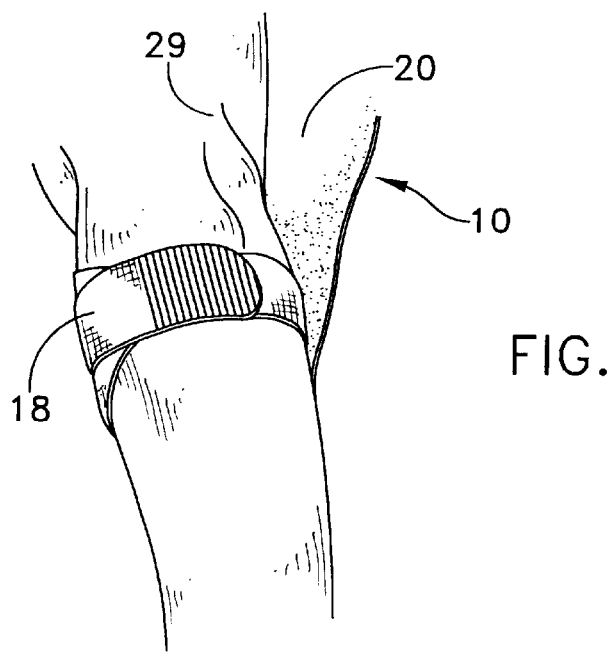
FIGS. 1F, 1G and 1H are top perspective views showing the orthopedic bandage of FIG. 1 being wrapped around an elbow such that the wider and narrower portions engage and overlap.
Figure 1G:
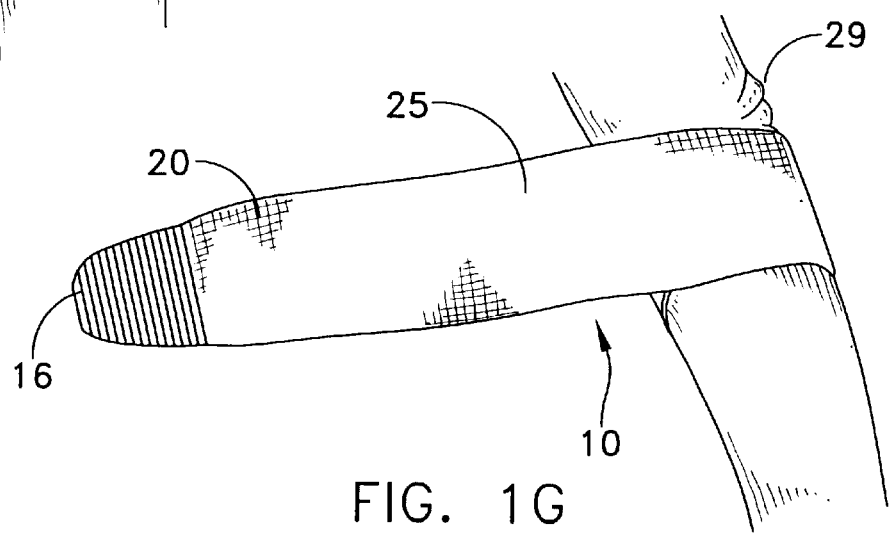
Figure 1H:
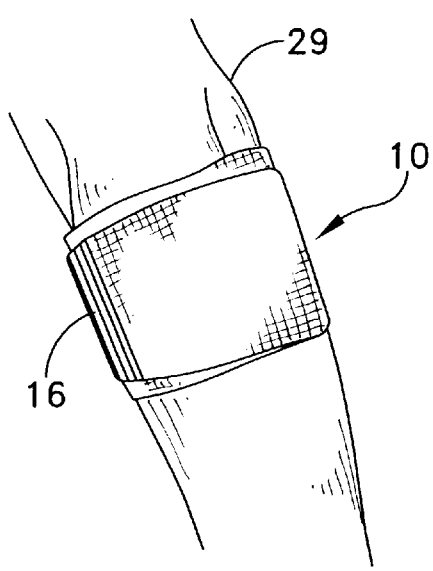

FIGS. 1F, 1G and 1H show another alternative use of bandage 10 of FIG. 1 to concentrate the pressure exerted on a more or less cylindrical anatomical part, such as a forearm near an elbow. The wider section of bandage 10 exerts a distributed force and/or acts as an outer pad; and the narrower section of bandage 10 exerts a concentrated force which may be selected by the user. As shown in FIG. 1F and 1G, when wrapping bandage 10 around elbow 29, first end 18 threaded through transverse opening 22 (not shown) and tab 16 of first end 18 is secured to a receiving surface defined by the portion of fabric layer 12. FIG. 1H shows second end 20 of bandage 10 (wider section), wrapped completely around the forearm near the elbow 29 with tab 16 secured to the receiving surface defined by a portion of fabric layer 12 that is facing the wider section of bandage 10, and which section overlies the affixed narrower strap section.

Figure 3:
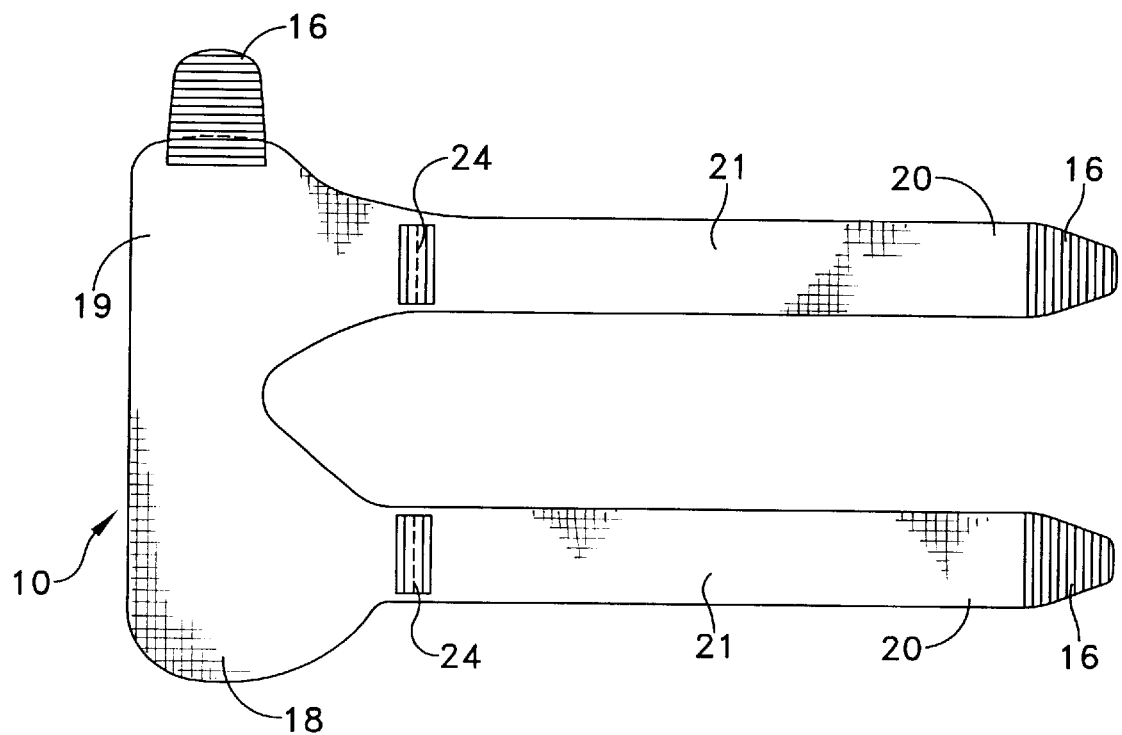
FIG. 3 is a top plan view of a modified embodiment of a foam plastic orthopedic bandage of the invention.

FIG. 3 shows another application of combined wide and narrow pads/straps in a bandage according to the invention. This bandage 10 is generally U-shaped with a singular wide body 19 having a fastener tab 16 that wraps in a first direction to engage a first end 18, and two legs 21 leading to tabs 16 at a second end 20, the legs being arranged to wrap in a second direction substantially perpendicular to the first. This embodiment advantageously is applied to joints that may be arranged at a right angle, such as the ankle or elbow.

In FIGS. 3A, 3B, 3C and 3D, the wide portion of bandage 10 is wrapped over the instep of a foot 26, and the narrower strap portions of bandage 10, which are arranged symmetrically, are crossed behind the ankle, e.g., over the Achilles tendon. The narrow straps are brought forward such that their tabs 16 attach on the surface of fabric layer 12 of the wider portion, now affixed around the foot.

Figure 3A:
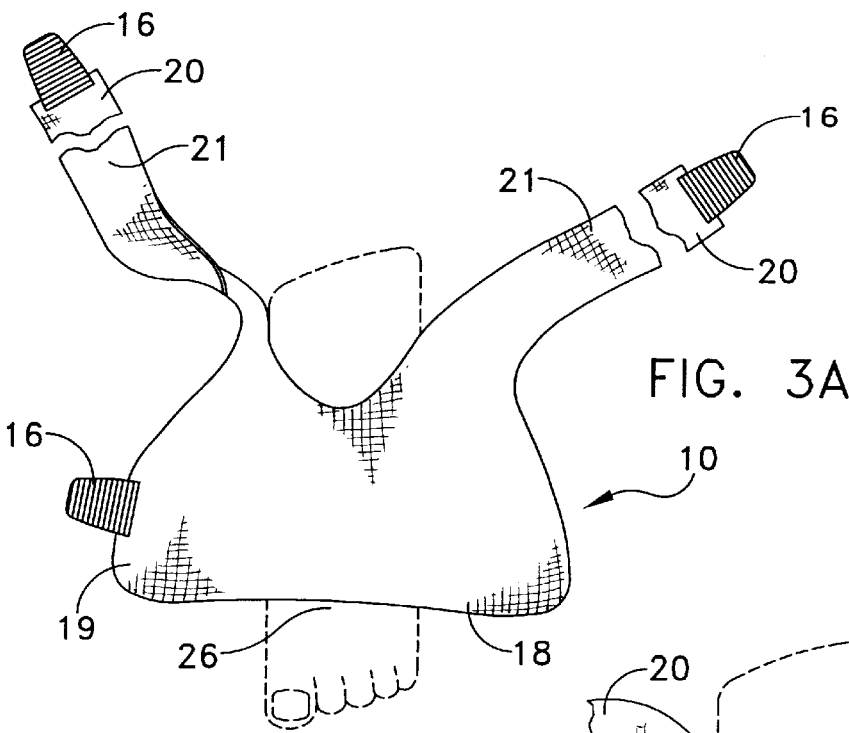
FIGS. 3A, 3B, 3C and 3D are top plan views showing the orthopedic bandage of FIG. 3 being wrapped around a foot and ankle.
Figure 3B:
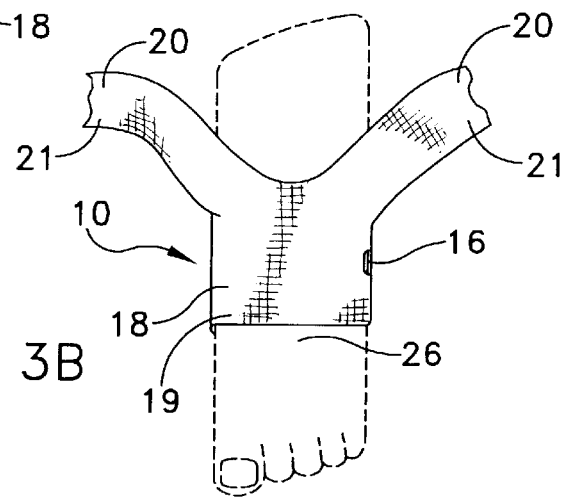
Figure 3C:
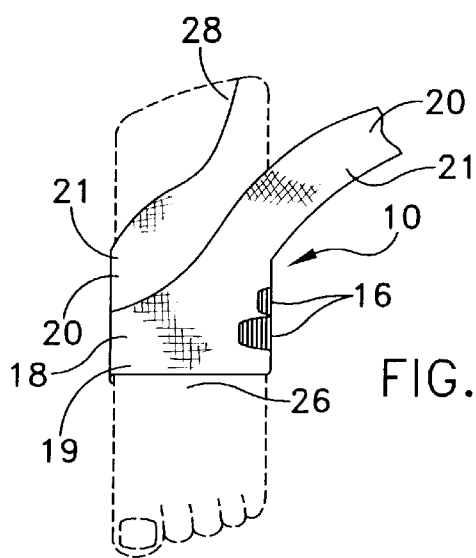
Figure 3D:
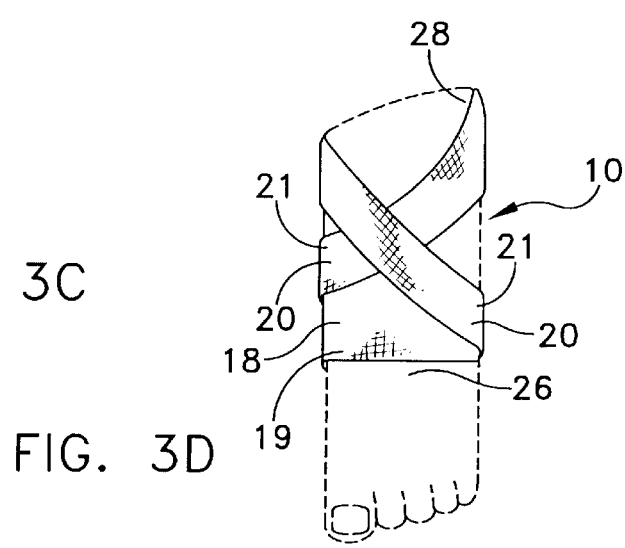

Referring to FIG. 3A, bandage 10 is shown partially wrapped around foot 26. FIG. 3B shows singular body 19 of first end 18 wrapped around foot 26 and tab 16 of first end 18 secured to the receiving surface of first end 18, at a specific position determined by the degree of tightness required by the wearing. FIG. 3C shows one leg 21 of second end 20 wrapped around ankle 28 and foot 26 and tab 16 on one leg 21 of second end 20 secured to the receiving surface of first end 18. FIG. 3D. shows the other leg 21 of second end 20 wrapped around ankle 28 and foot 26 and tab 16 (not shown) on the other leg 21 of second end 20 secured to the receiving surface adjacent to first end 18. Bandage 10 is shown completely wrapped and affixed around ankle 28 and foot 26.

Singular body 19 also can be wrapped around a vertical axis, forwardly, from behind the ankle and around foot 26. The two legs 21 of bandage 10 are wrapped around and cross-over foot 26. In any event, bandage 10 wraps around ankle 28 and foot 26 of the wearer, in this example, or around the humerus and radius/ulna at the elbow, etc.

In FIGS. 3E, 3F, 3G and 3H, the wide portion of bandage 10 is wrapped over the Achilles tendon 32, heel and ankle 28 areas of a foot 26, and the narrower strap portions of bandage 10, which are arranged symmetrically, are crossed over the instep of a foot 26. The narrow straps are brought forward such that their tabs 16 attach on the surface of fabric layer 12 of either the wider portion or the narrow portion, both now affixed around the foot and ankle.

Figure 3E:
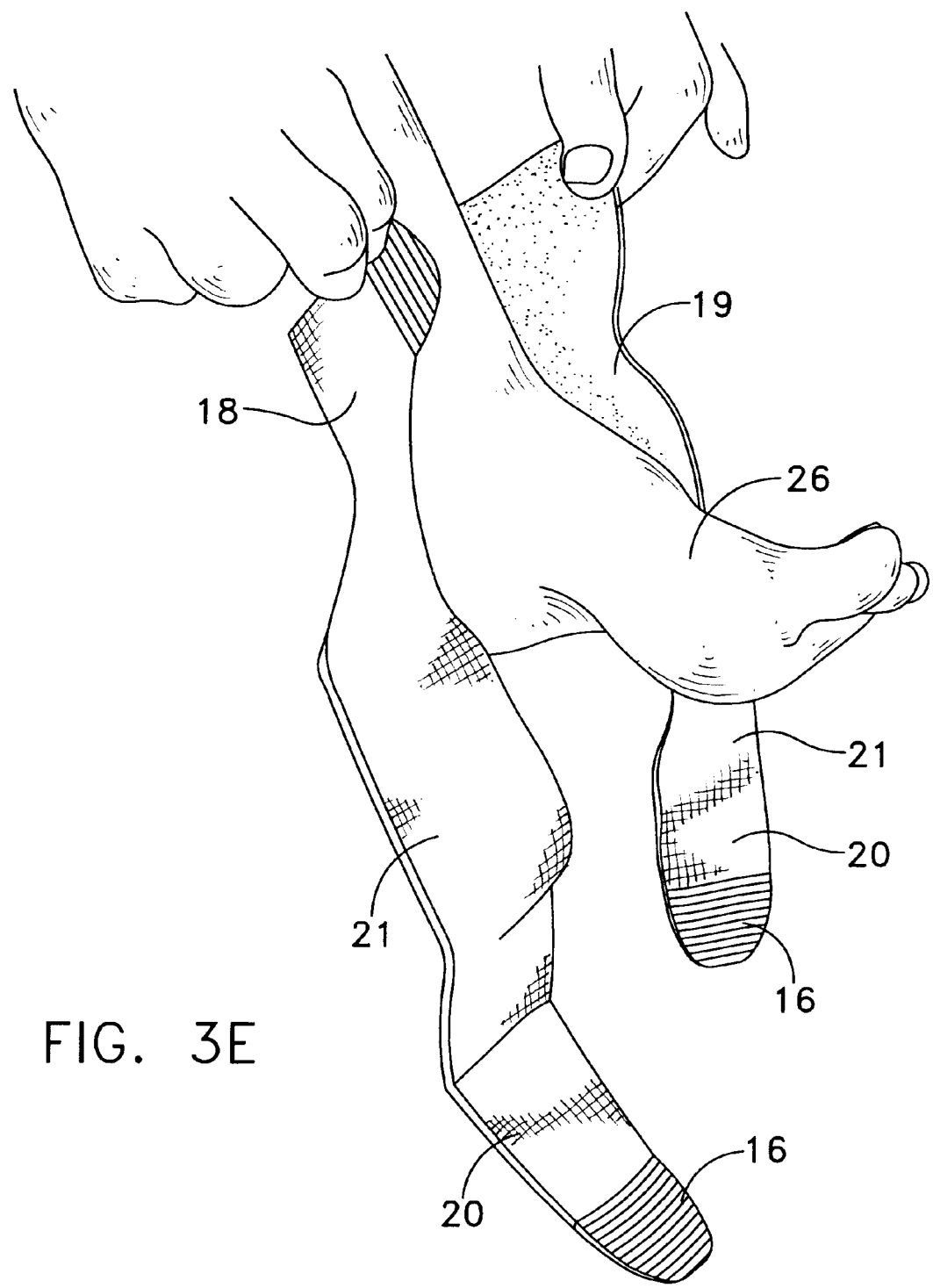
FIGS. 3E, 3F, 3G and 3H are perspective views showing the orthopedic bandage of FIG. 3 being wrapped around a foot and ankle.
Figure 3F:
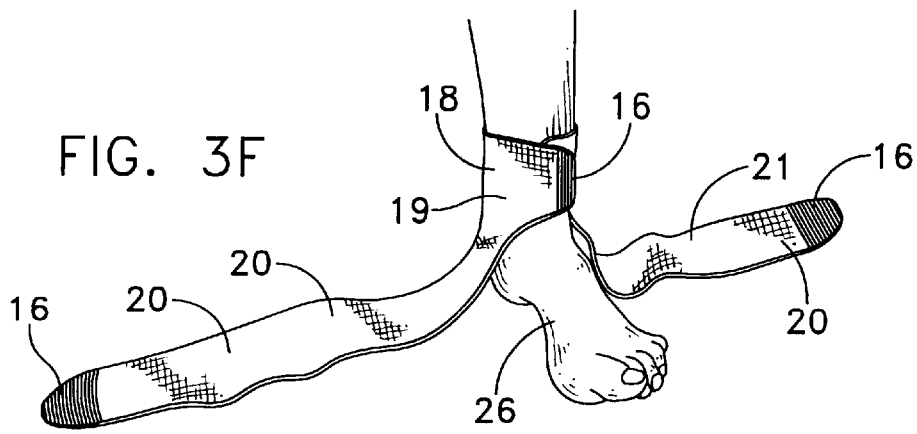
Figure 3G:
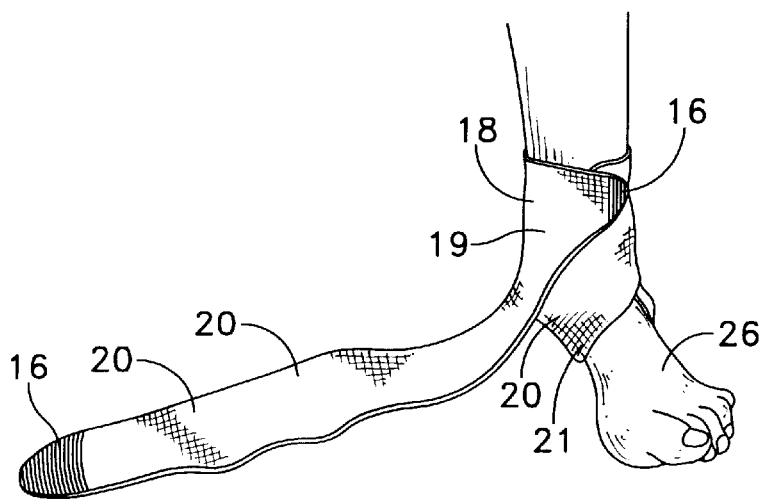
Figure 3H:
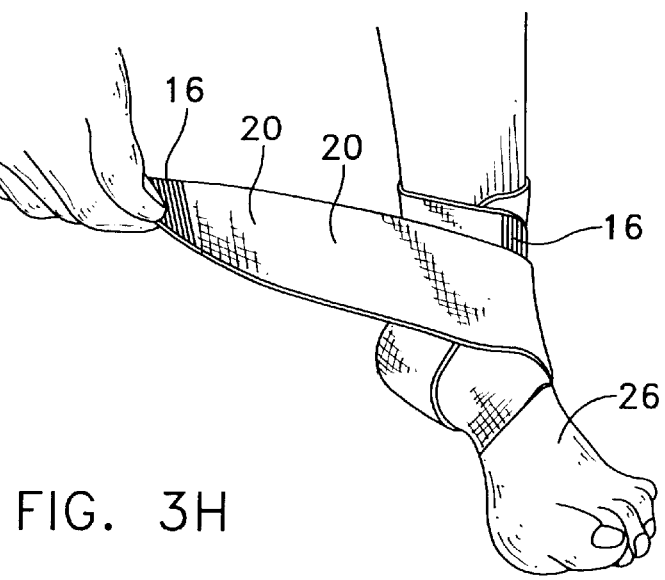

Referring to FIG. 3E, bandage 10 is shown partially wrapped around foot 26. FIG. 3F shows singular body 19 of first end 18 wrapped around ankle 28 and tab 16 of first end 18 secured to the receiving surface of first end 18, at a specific position determined by the degree of tightness required by the wearing. FIG. 3G shows one leg 21 of second end 20 wrapped around foot 26 and ankle 28 and tab 16 (not shown) on one leg 21 of second end 20 secured to the receiving surface of first end 18. FIG. 3H shows the other leg 21 of second end 20 wrapped around ankle 28 and foot 26 and tab 16 (not shown) on the other leg 21 of second end 20 secured to the receiving surface adjacent to first end 18. Bandage 10 is shown completely wrapped and affixed around ankle 28 and foot 26.

According to the foregoing embodiments, wide and narrow pads/straps are permanently affixed, end to end, either by having been integrally cut from the same sheet (e.g., FIGS. 1, 7) or having attached separate parts (e.g., FIGS. 3, 6, 8 and 9). For example, in FIG. 3, electrically welded bridging tabs 24 affix the narrow legs to the wider singular part. As an alternative, the wide and narrow sections can be separably attached using hook type fastener tabs.

Figure 4:
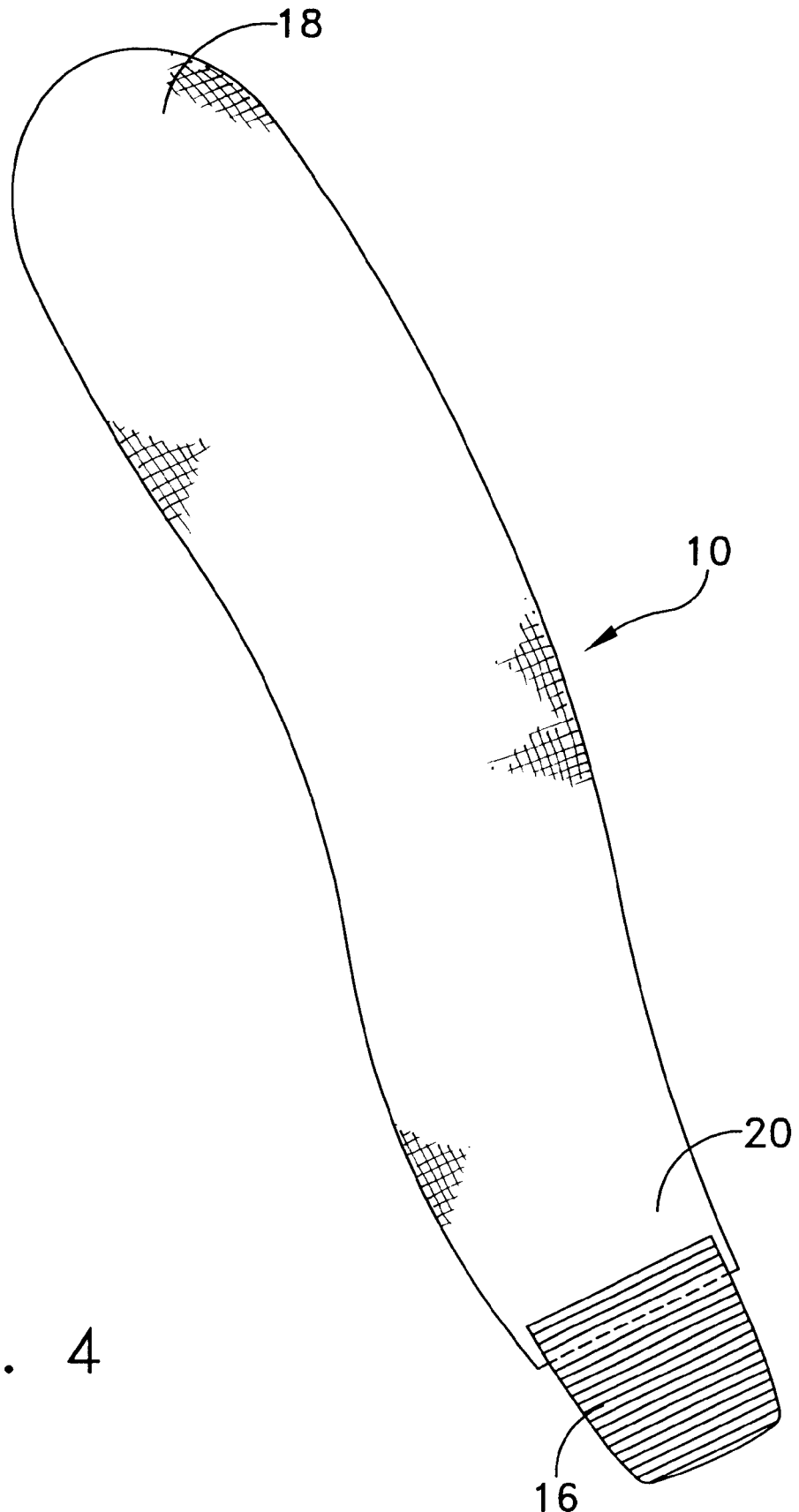
FIG. 4 is a perspective view of another modified embodiment of the foam plastic orthopedic bandage.
Figure 4A:
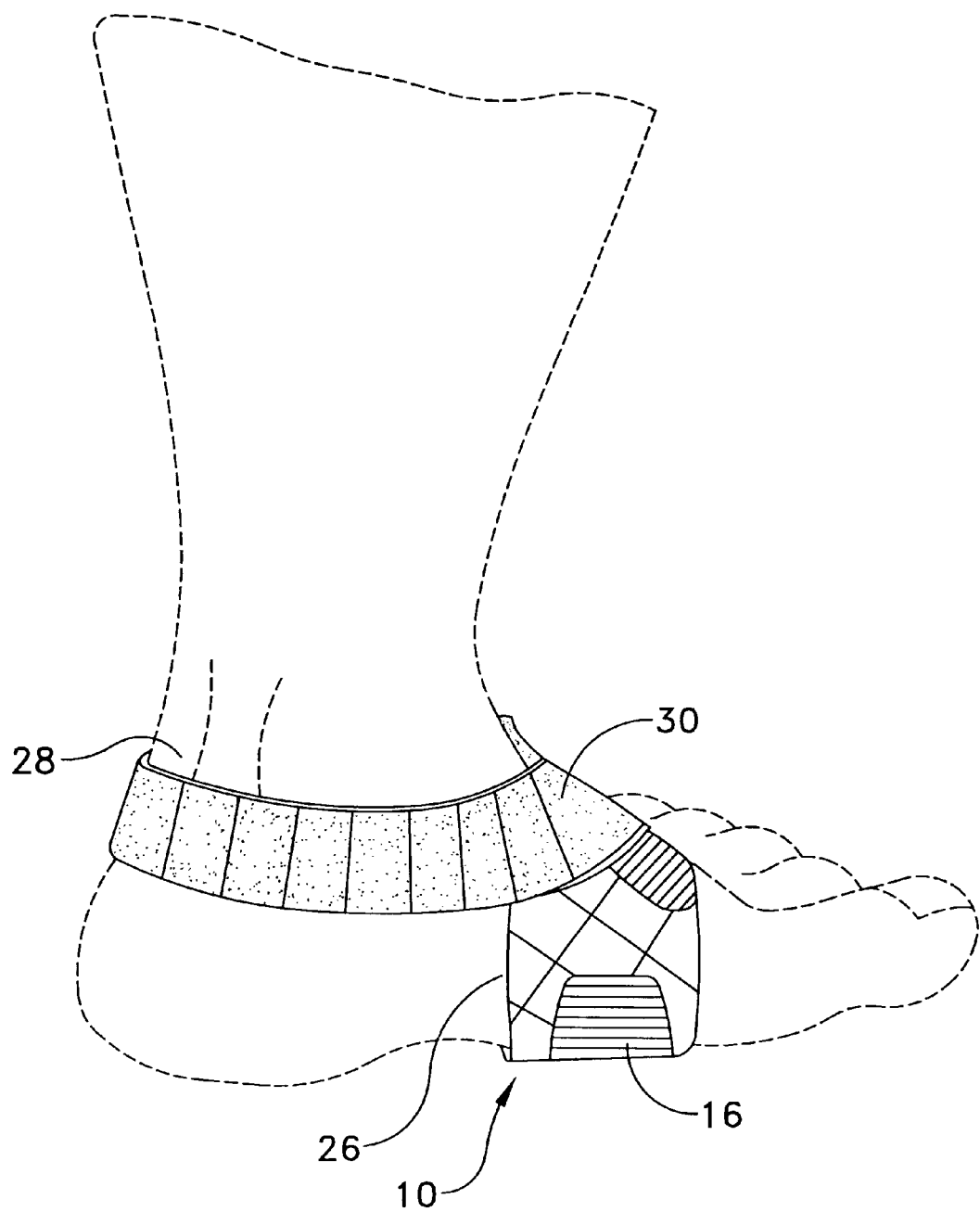
FIG. 4A is a perspective view showing the orthopedic bandage of FIG. 4 being wrapped around a foot and being used in combination with a similar but narrower bandage wrapped around an ankle, to support the arch, subtalor joint and the Achilles tendon.

FIG. 4 shows the basic unit of the bandage having a fabric faced, foam body and a hook-type fastener tab 16 attached thereto. This basic unit can be relatively wide and short and used together with an otherwise similar unit that is relatively long and narrow, thereby achieving even more versatility than in the previous embodiments. Furthermore, as suggested in FIG. 4, bandage 10 can have a part which is non-linear from first end 18 to second end 20. In this case, one side is substantially concave and one side is substantially convex, as viewed from first end 18 to second end 20. Combining the aspects of non-linear shape and the use of wider and narrower segments, as shown in FIG. 4A, bandage 10 can be wrapped around a joint in which there is a transition from one shape to another. In FIG. 4A, the wider non-linear shape complements the generally elliptical and tapering shape of foot 26 with tab 16 securing this part to the receiving surface of bandage 10. One or more narrower straps are wrapped around the ankle and have a tab 16 that preferably is affixed to the receiving fabric surfaces of both the wide and narrow parts.

Figure 5:
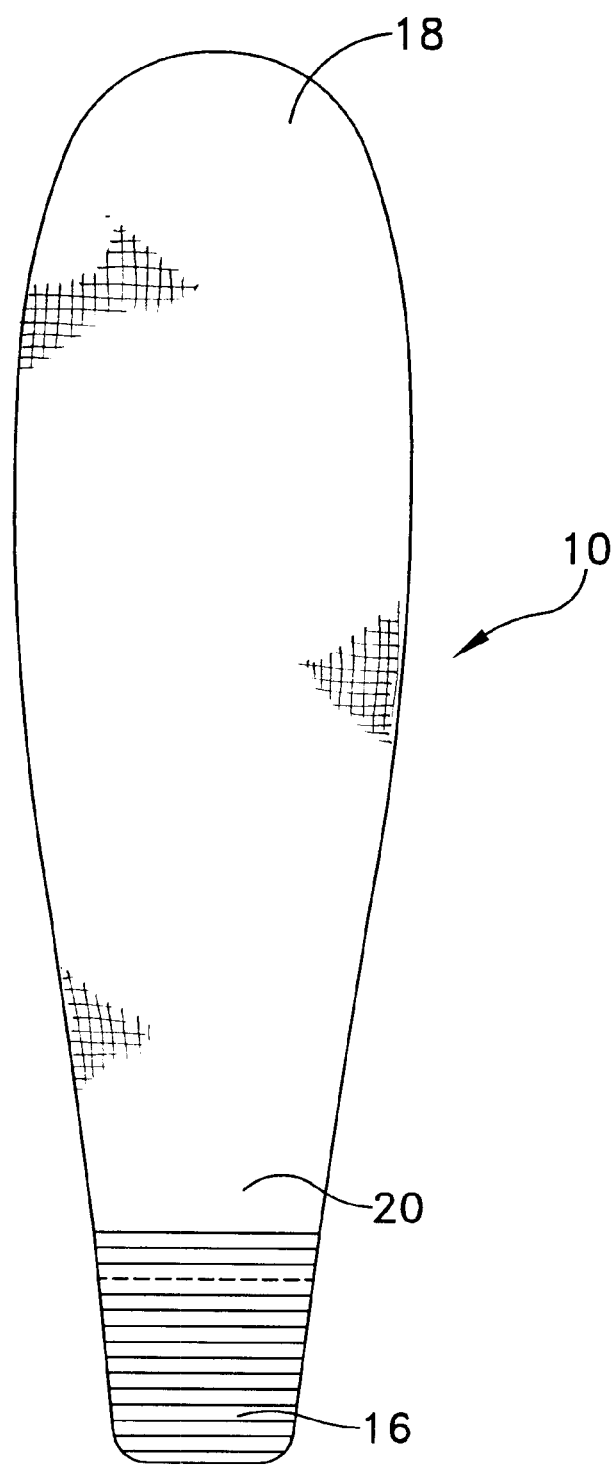
FIG. 5 is a top perspective view of another alternative embodiment of the foam plastic orthopedic bandage.
Figure 5A:
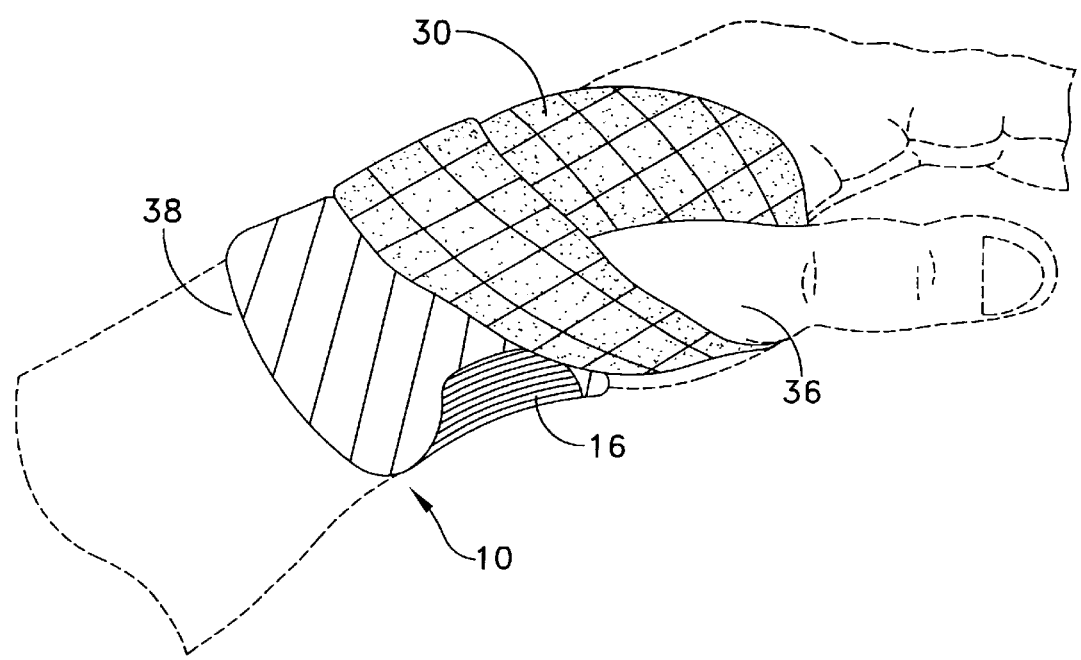
FIG. 5A is a perspective view showing the orthopedic bandage of FIG. 5 as wrapped around a wrist and used in combination with another similar but narrower bandage wrapped obliquely to engage around a thumb.

FIGS. 5 and A show a similar embodiment, as applied to a hand and wrist. This embodiment of bandage 10 is also non-linear from first end 18 to second end 20, but is symmetrical, in that both sides are generally tapered toward one another from first end 18 to the second end 20. As seen in FIG. 5A, bandage 10 may be wrapped around a wrist 38 and tab 16 secured to the receiving surface of bandage 10. A similar but narrower orthopedic bandage 30 is wrapped around a thumb 36 to provide additional support, as well as to hold the wider part forwardly against the rearward taper of the hand.

Figure 6:
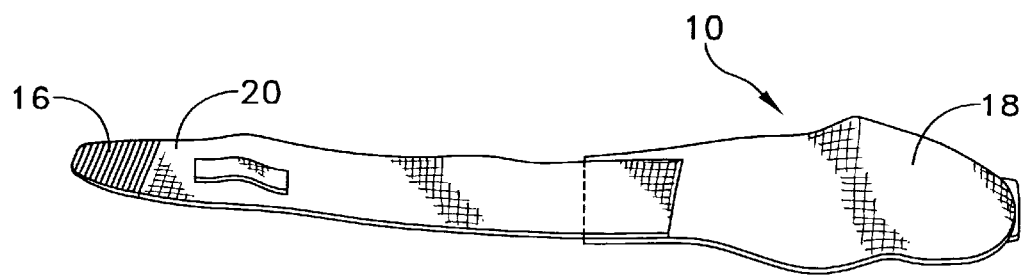
FIG. 6 is a top plan view of another alternative embodiment of the foam plastic orthopedic bandage of the invention.
Figure 6A:
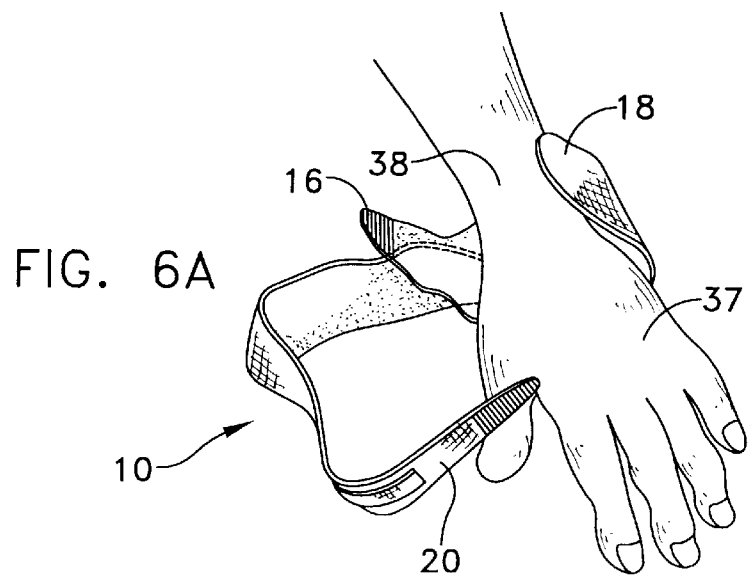
FIGS. 6A, 6B, 6C and 6D are top perspective views showing the orthopedic bandage of FIG. 6 being wrapped around a wrist such that the wider and narrower portions engage and overlap.
Figure 6B:
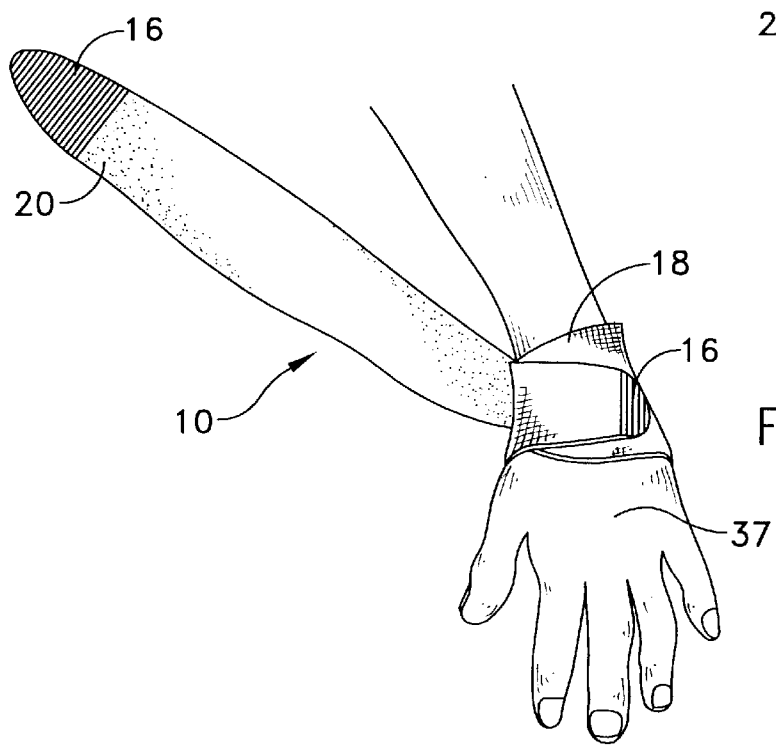
Figure 6C:
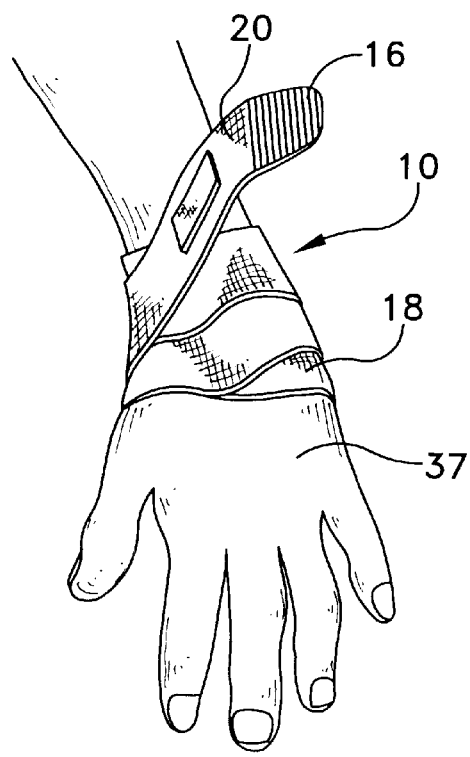
Figure 6D:
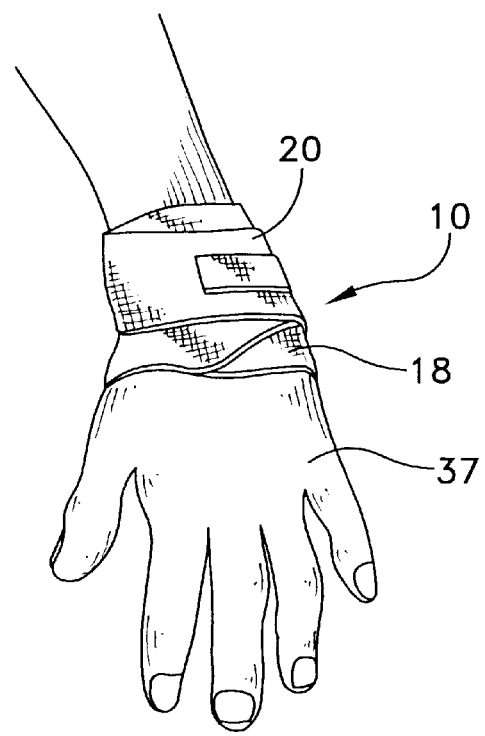

FIGS. 6, 6A, 6B, 6C and 6D show an alternative use of bandage 10 to concentrate the pressure exerted on a more or less cylindrical anatomical part, such as a wrist 38 or forearm. The wider section of bandage 10 exerts a distributed force and/or acts as an inner pad; and the narrower section of bandage 10 exerts a concentrated force which may be selected by the user. FIG. 6A, shows the initial placement of the wider section of bandage 10 around wrist 38. FIG. 6B shows the first closure of the wider section and the initial wrapping of the narrower section around wrist 38. As shown in FIG. 6B, when wrapping bandage 10 around wrist 38, first end 18 of bandage 10 and tab 16 of first end 18 is secured to a receiving surface defined by the wider section of fabric layer 12. FIG. 6C shows the narrower section of bandage 10 being pulled for compression around the general wrist area. FIG. 6D shows the second end 20 of bandage 10 (narrower section), wrapped completely around wrist 38 with tab 16 (not shown) secured to the receiving surface defined by a portion of fabric layer 12 of the narrower section of bandage 10, and which section overlies the affixed wider strap section.

Figure 7:
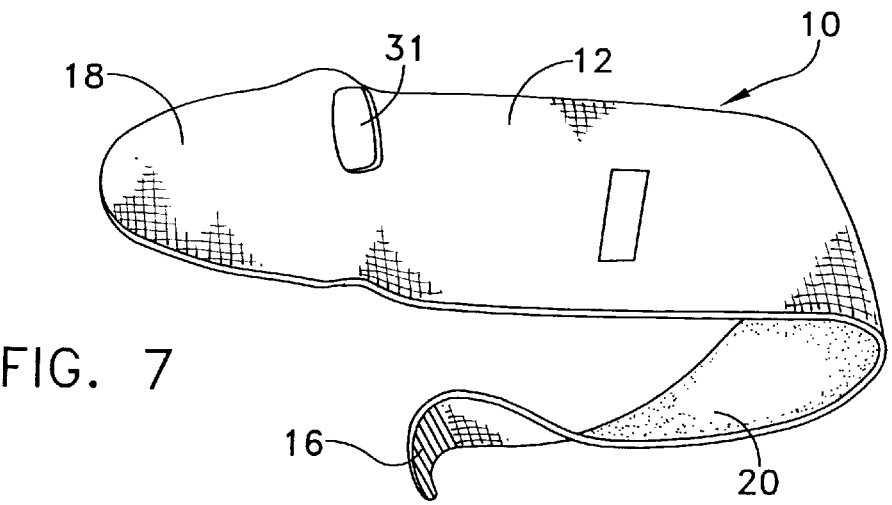
FIG. 7 is a top perspective view of a fabric-side of another alternative embodiment of a foam plastic orthopedic bandage of the invention.
Figure 7A:
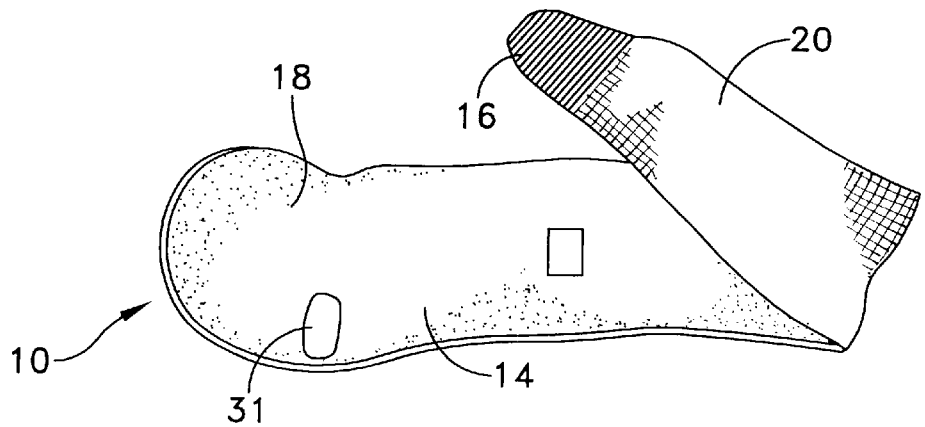
FIG. 7A is a top perspective view of a foam-side of another alternative embodiment of a foam plastic orthopedic bandage of FIG. 7.
Figure 7B:
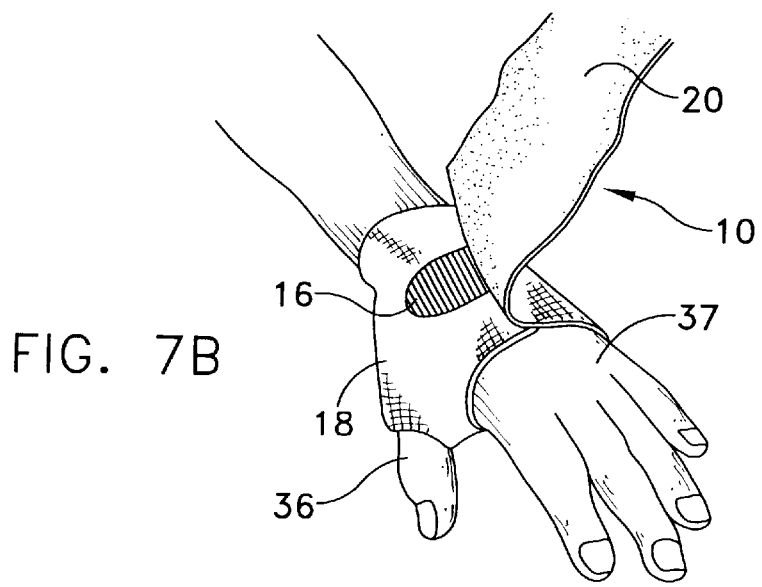
FIGS. 7B, 7C, 7D and 7E are perspective views showing the orthopedic bandage of FIG. 7 being wrapped around a hand, wrist and thumb for relieving carpal tunnel syndrome by providing support in the region of the wrist.
Figure 7C:
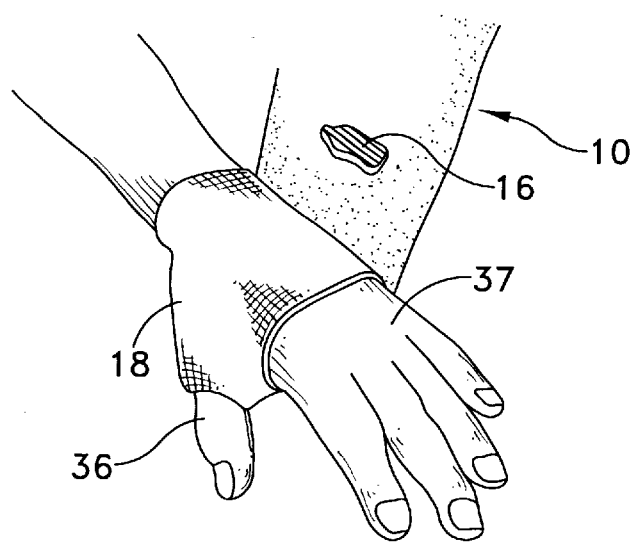
Figure 7D:
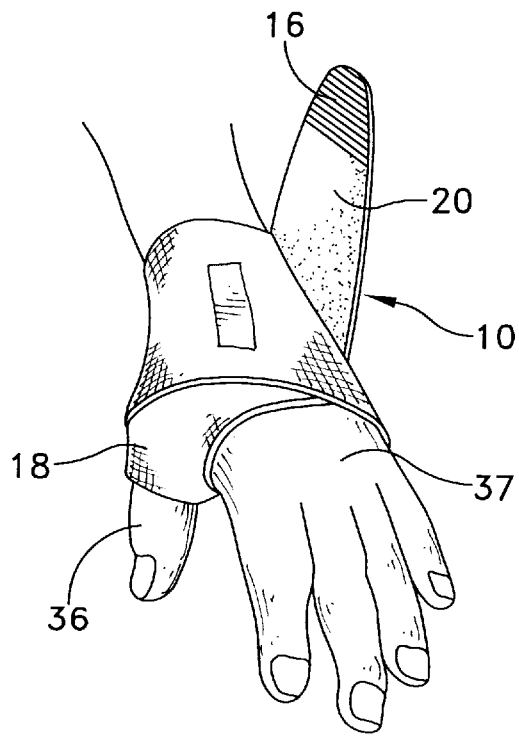
Figure 7E:
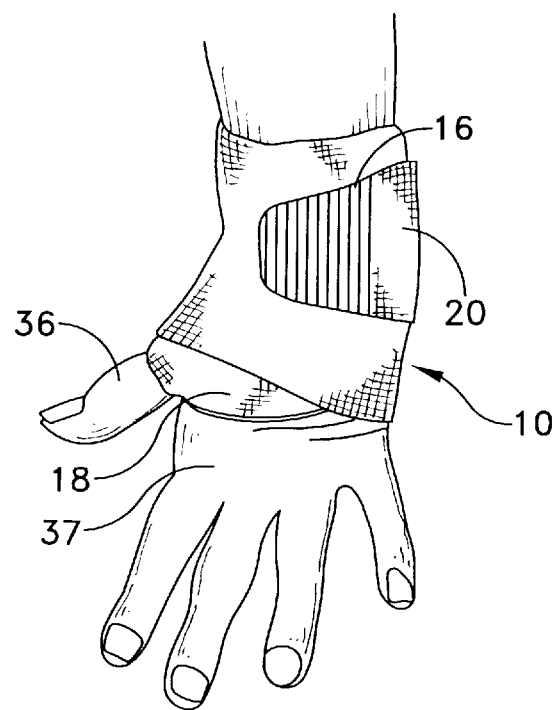

FIGS. 7, 7A, 7B, 7C, 7D and 7E show bandage 10 being wrapped around a hand 37, wrist 38 and thumb 36, similar to FIG. 5. FIG. 7 shows a view of the fabric-side and FIG. 7A shows a view of the foam-side of the foam plastic orthopedic bandage of FIG. 7. This embodiment of bandage 10 is also non-linear from first end 18 to second end 20 and generally tapers from the wider first end 18 to the narrower second end 20. In addition, bandage 10 is diagonally opposed generally from first end 18 to second end 20 and an opening 31 is formed in bandage 10 in said wider portion, said opening 31 being located off-center. As seen in FIG. 7B, bandage 10 is worn like a glove around a hand 37 and shows bandage 10 being closed. In contrast, FIG. 7C shows the bandage before the glove portion is actually closed. FIG. 7D shows bandage 10 being pulled for compression around the general hand area. FIG. 7E shows the second end 20 of bandage 10 wrapped completely around hand 37 with tab 16 secured to the receiving surface defined by a portion of fabric layer 12 of the second end 20 of bandage 10, and which section overlies the affixed glove strap section.

Figure 8:
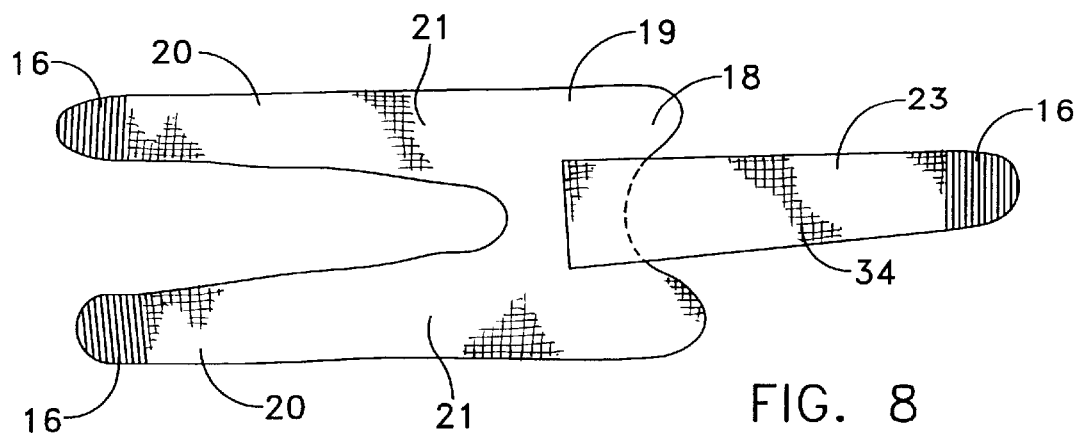
FIG. 8 is a top perspective view of another alternative embodiment of the foam plastic orthopedic bandage, specifically for restraining the position of the patella while otherwise permitting substantial knee joint mobility.
Figure 8A:
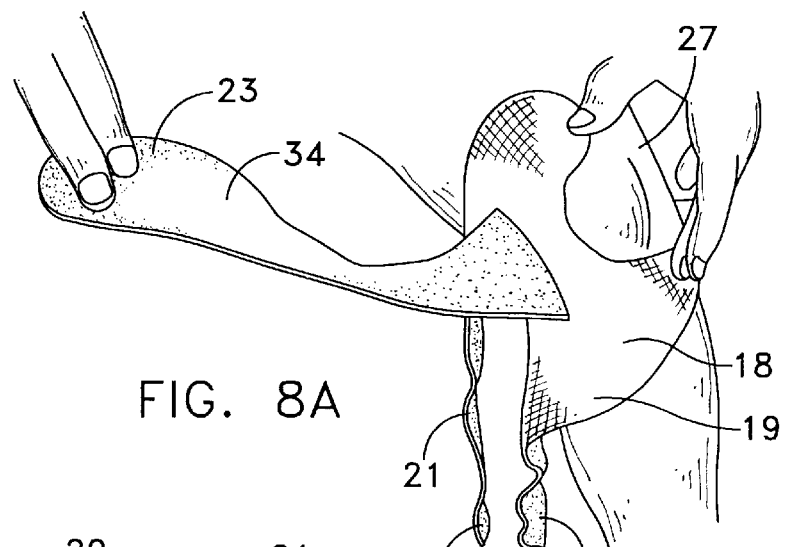
FIGS. 8A, 8B, 8C, 8D, 8E and 8F are perspective views showing the orthopedic bandage of FIG. 8 being wrapped around a knee.
Figure 8B:
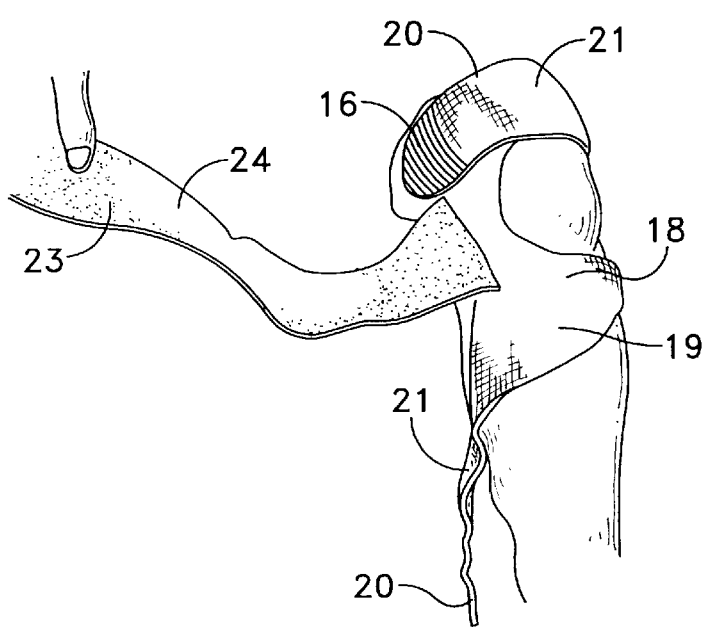
Figure 8C:
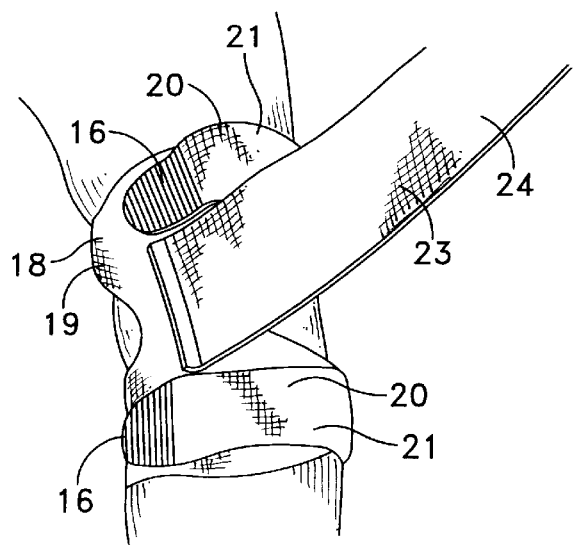
Figure 8D:
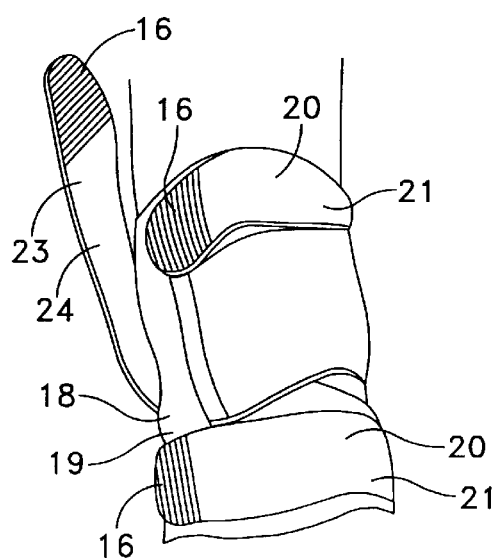
Figure 8E:
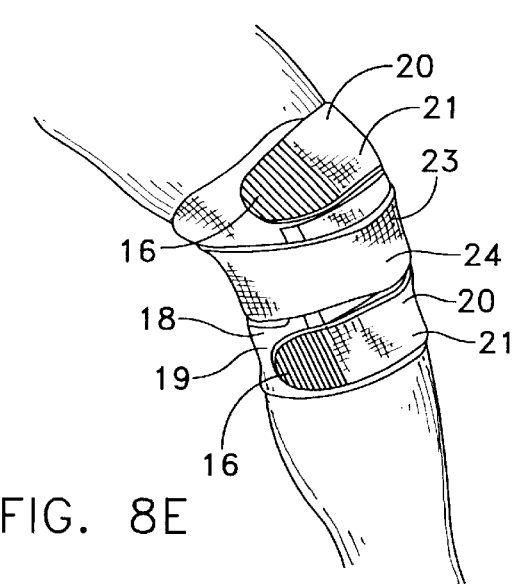
Figure 8F:
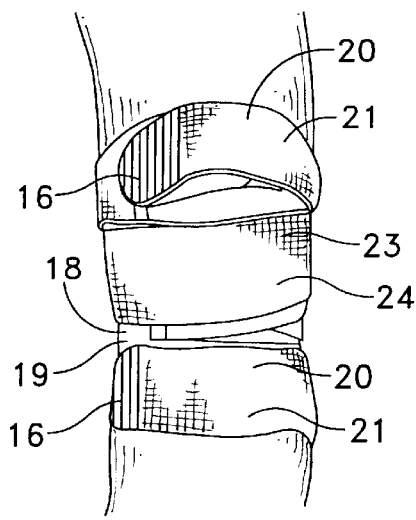

FIG. 8 shows the invention in an embodiment combining the aspects of wide and narrow pads/straps in a bandage. This bandage is generally U-shaped with a singular wide body 19 having a fastener tab 16 that wraps in a first direction to engage a first end 18, two legs 21 leading to tabs 16 at a second end 20, and a single leg 34 leading to tabs at a third end 23. This embodiment is advantageously applied around a knee 27. FIGS. 8A, 8B, 8C, 8D, 8E and 8F are perspective views showing the orthopedic bandage of FIG. 8 being wrapped around a knee 27. The bandage is adjustable in tension to apply gradient pressure for securely positioning the patella, namely by defining a fixed at-least-partial enclosure surrounding the crown of the patella, but not substantially impeding the mobility of the knee joint as a whole. FIG. 8A shows initial placement of the first end 18 having a singular wide body 19, around a knee 27. FIG. 8B shows the closure of one of the two legs 21 of the second end 20 around the knee with the tab 16 of one leg of the second end 20 secured to a receiving surface defined by the first leg of the second end 20 of fabric layer 12. FIG. 8C similarly shows the closure of the second of the two legs 21 of the second end 20 around the knee 27 with the tab of the second leg of the second end 20 secured to a receiving surface defined by the second leg of the second end 20 of fabric layer 12. FIG. 8D additionally shows the single leg 22 of the third end being pulled for compression around the knee cap area. Referring to FIG. 8D, the single leg 24 of the third end 23 of the bandage is being pulled for compression behind the knee cap area. FIG. 8E is a side view of the embodiment, showing the single leg 34 of the third end 23 of the bandage wrapped completely around the knee 27 area with tab 16 (not shown) secured to a receiving surface defined by the single leg 34 of the third end 23 of fabric layer 12. FIG. 8F is a front view of the embodiment shown in FIG. 8E.

Figure 9:
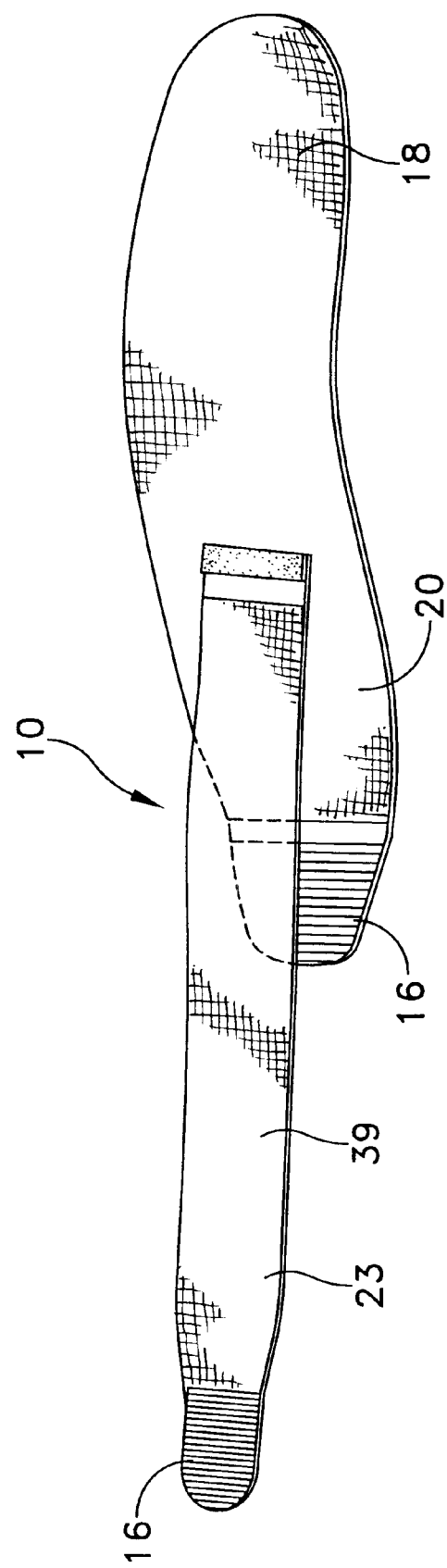
FIG. 9 is a top perspective view of another alternative embodiment of the foam plastic orthopedic bandage; and, FIGS. 9A, 9B and 9C are perspective views showing the orthopedic bandage of FIG. 9 being wrapped around a foot and Achilles tendon.
Figure 9A:
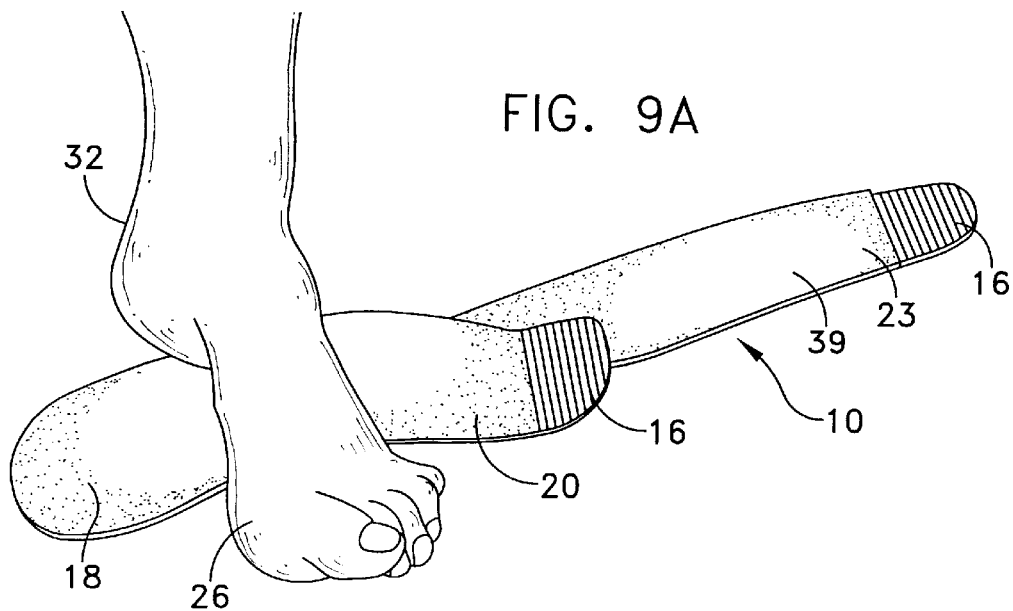
Figure 9B:
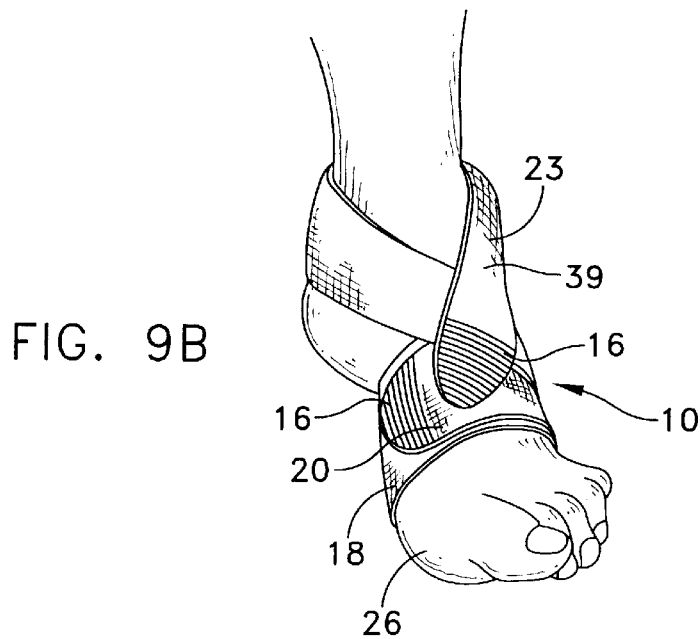
Figure 9C:
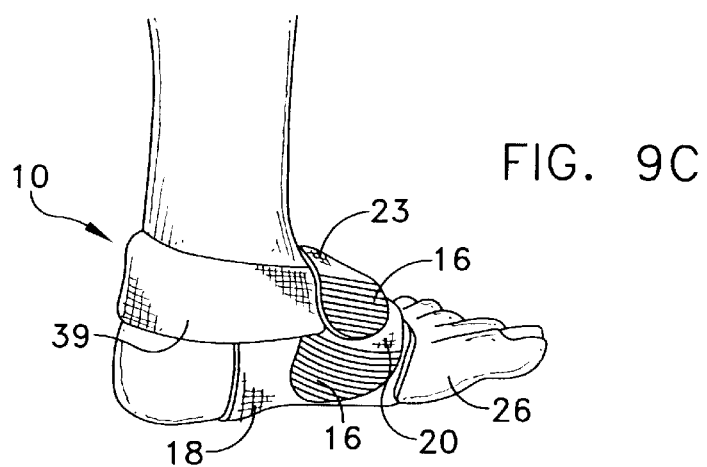

FIG. 9 shows a bandage 10 combining the aspects of non-linear shape and the use of wider and narrower segments. As suggested in FIG. 9, bandage 10 can have a part which is non-linear from first end 18 to second end 20. In this case, one side is substantially concave and one side is substantially convex, as viewed from first end 18 to second end 20. Combining the aspects of non-linear shape and the use of wider and narrower segments, as shown in FIG. 9A, bandage 10 can be wrapped around a joint in which there is a transition from one shape to another. As shown in FIGS. 9B and 9C, the wider non-linear shape complements the generally elliptical and tapering shape of foot 26 with tab 16 securing this part to the receiving surface of bandage 10. The affixed narrower linear strap 39 is wrapped around the Achilles is tendon 32 and have a tab 16 that preferably is affixed to the receiving fabric surfaces of both the wide and narrow parts. FIG. 9A, shows the initial placement of the wider non-linear section of bandage 10 underneath foot 26. FIG. 9B shows the closure of the wider section around foot 26 and the narrower section 39 around Achilles tendon 32.

As shown in FIG. 9B, when wrapping bandage 10 around foot 26, second end 20 of bandage 10 and tab 16 of second end 20 is secured to a receiving surface defined by the wider first end 18 of fabric layer 12. Also shown in FIG. 9B, when wrapping bandage 10 around Achilles tendon 32, third end 23 of bandage 10 and tab 16 of third end 23 is secured to the receiving surfaces defined by the wider section and the narrower section of fabric layer 12. FIG. 9C shows a side perspective view of FIG. 9B. FIGS. 9B and 9C show the third end 23 of bandage 10 (narrower section 39), wrapped completely around Achilles tendon 32 with tab 16 secured to the receiving surface defined by a portion of fabric layer 12 of the narrower section 39 and the wider section of bandage 10, and which narrower section 39 overlies the affixed wider strap section.

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

What is claimed is:

1. A bandage comprising:

a fabric layer having a first end and a second end, said fabric defining an operative surface of a hook and loop fastener;

a layer of elastomeric foam bonded to said fabric layer on the side opposite from said operative surface;

hook means extending from an edge of said fabric, said hook means being engageable with said fabric layer and operable to releasably attach portions of said bandage together;

having at least two sections comprising different widths between said first and second ends; and, wherein the bandage defines a channel having a singular body at a bottom of said channel and two legs extending from said singular body for wrapping said legs in a first direction, said hook means including a first hook tab at a free end of each of said legs and a second hook tab on a lateral edge of said singular body for wrapping said singular body in a second direction that is substantially perpendicular to said first direction.

2. The bandage according to claim 3, wherein a portion of said bandage between said first end and said second end is wider than said first end and a transverse opening is formed in said bandage in said wider portion, said opening being at least as wide as said first end whereby said first end may be wrapped around a body member and threaded through said opening.

3. The bandage according to claim 1, wherein the portion of said bandage between said first end and said second end and one side is generally concave and an opposite side is generally convex from said first end to said second end, whereby said bandage may be wrapped around a tapering anatomical part.

4. The bandage according to claim 3, further comprising a narrow strap portion having a layer of said fabric defining a receiving surface that is engageable with said hooks, a layer of elastomeric foam bonded to said fabric layer, and hook means extending therefrom, said narrow strap portion attaching at least partly to said bandage, whereby said bandage can engage a tapering anatomical part.

5. The bandage according to claim 4, wherein said narrow strap portion attaches at least partly to said bandage.

6. The bandage according to claim 1, wherein said bandage is non-linear from said first end to said second end and defining sides that are generally concave and tapered from said first end to said second end.

7. The bandage according to claim 6, further comprising a narrow strap portion having a layer of said fabric defining a receiving surface that is engageable with said hooks, a layer of elastomeric foam bonded to said fabric layer, and hook means extending therefrom, said n arrow strap portion attaching at least partly to said bandage, whereby said bandage can engage a generally cylindrical anatomical part.

8. The bandage according to claim 7, wherein said narrow strap portion attaches at least partly to said bandage.

9. The bandage according to claim 1, wherein said bandage is non-linear from said first end to said second end and defining sides that are generally concave and tapered from said first end to said second end, and said bandage being diagonally opposed generally from said first end to said second end, and an opening being formed in said bandage in said wider portion, said opening being located off-center.

10. A bandage comprising:
  a fabric layer having a first end and a second end, said fabric defining an operative surface of a hook and loop fastener;
  a layer of elastomeric foam bonded to said fabric layer on the side opposite from said operative surface;
  hook means extending from an edge of said fabric, said hook means being engageable with said fabric layer and operable to releasably attach portions of said bandage together;
  having at least two sections comprising different widths between said first and second ends; and,
  wherein said bandage is non-linear from said first end to said second end and defining sides that are generally concave and tapered from said first end to said second end, and said bandage being diagonally opposed generally from said first end to said second end, and an opening being formed in said bandage in said wider portion, said opening being located off-center; and,
  further comprising additional hook means located between said first end and said second end, said hook means being engageable with said fabric layer of a portion of said first end and operable to releasably attach said portion to portions of said bandage together.

11. A bandage comprising:
  a fabric layer having a first end and a second end, said fabric defining an operative surface of a hook and loop fastener;
  a layer of elastomeric foam bonded to said fabric layer on the side opposite from said operative surface;
  hook means extending from an edge of said fabric, said hook means being engageable with said fabric layer and operable to releasably attach portions of said bandage together;
  having at least two sections comprising different widths between said first and second ends; and,
  wherein the bandage defines a substantially channel-shaped body, having a singular body at a bottom of said channel and two legs extending from said singular body for wrapping said legs in a first direction, said hook means including a first hook tab at a free end of each of said legs, and a third leg extending from said singular body in a second direction generally diametrically opposed to said first direction for wrapping said third leg in said second direction, and said hook means including a second hook tab at a free end of said third leg.

12. The bandage according to claim 11, wherein a portion of said third leg attaches at least partly to said bandage.

* * * * *